(12) United States Patent
Hausner et al.

(10) Patent No.: US 8,440,222 B2
(45) Date of Patent: May 14, 2013

(54) RESERVOIR SYSTEM WITH CLOSED MEMBRANE

(75) Inventors: Heike Hausner, Holzkirchen (DE); Sebastian Braun, Hausham (DE); Heiko Spilgies, München (DE)

(73) Assignee: Acino AG, Miesbach (DE)

( * ) Notice: Subject to any disclaimer, the term of this patent is extended or adjusted under 35 U.S.C. 154(b) by 94 days.

(21) Appl. No.: 12/651,167

(22) Filed: Dec. 31, 2009

(65) Prior Publication Data

US 2010/0172959 A1 Jul. 8, 2010

Related U.S. Application Data

(63) Continuation of application No. PCT/DE2008/001112, filed on Jul. 4, 2008.

(30) Foreign Application Priority Data

Jul. 4, 2007 (DE) .......................... 10 2007 030 965

(51) Int. Cl.
| | |
|---|---|
| *A61F 13/00* | (2006.01) |
| *A61F 13/02* | (2006.01) |
| *A61K 9/70* | (2006.01) |
| *A61L 15/16* | (2006.01) |

(52) U.S. Cl.
USPC ............ 424/449; 424/443; 424/447; 424/448

(58) Field of Classification Search .................. None
See application file for complete search history.

(56) References Cited

U.S. PATENT DOCUMENTS

| | | | | |
|---|---|---|---|---|
| 3,797,494 | A | * | 3/1974 | Zaffaroni .................... 424/434 |
| 4,379,454 | A | | 4/1983 | Campbell et al. |
| 4,382,886 | A | * | 5/1983 | Sosnowski .................. 530/200 |
| 2002/0182260 | A1 | * | 12/2002 | Mak et al. .................... 424/522 |
| 2003/0060479 | A1 | * | 3/2003 | Brown et al. ................. 514/282 |
| 2004/0253299 | A1 | | 12/2004 | Beier et al. |

FOREIGN PATENT DOCUMENTS

| | | |
|---|---|---|
| CA | 1305384 C | 7/1992 |
| CA | 1338009 C | 1/1996 |
| GB | 2402884 A | 12/2004 |
| WO | 9932095 A | 7/1997 |
| WO | 0047208 A | 8/2000 |
| WO | 0059483 A | 10/2000 |
| WO | WO 2007112287 A2 * | 10/2007 |

OTHER PUBLICATIONS

Chandra et al., A Textbook of Dental Materials with Multiple Choice Questions, 2000, Jaypee Brothers Medical Publishers, First Ed., p. 84.*
International Search Report (PCT/DE2008/001112, 3 pages).
International Search Report (PCT/DE2008/001112, 3 pages), mailed on Nov. 13, 2008.

* cited by examiner

*Primary Examiner* — Carlos Azpuru
*Assistant Examiner* — Casey Hagopian
(74) *Attorney, Agent, or Firm* — The Maxham Firm

(57) ABSTRACT

A dermal or transdermal therapeutic system comprising a reservoir that contains at least one active substance, an active substance-permeable membrane which delimits the active-substance reservoir, and a closing layer. The closing layer is impermeable to the active substance at a temperature lying below the skin temperature while being permeable at skin temperature and above.

12 Claims, 1 Drawing Sheet

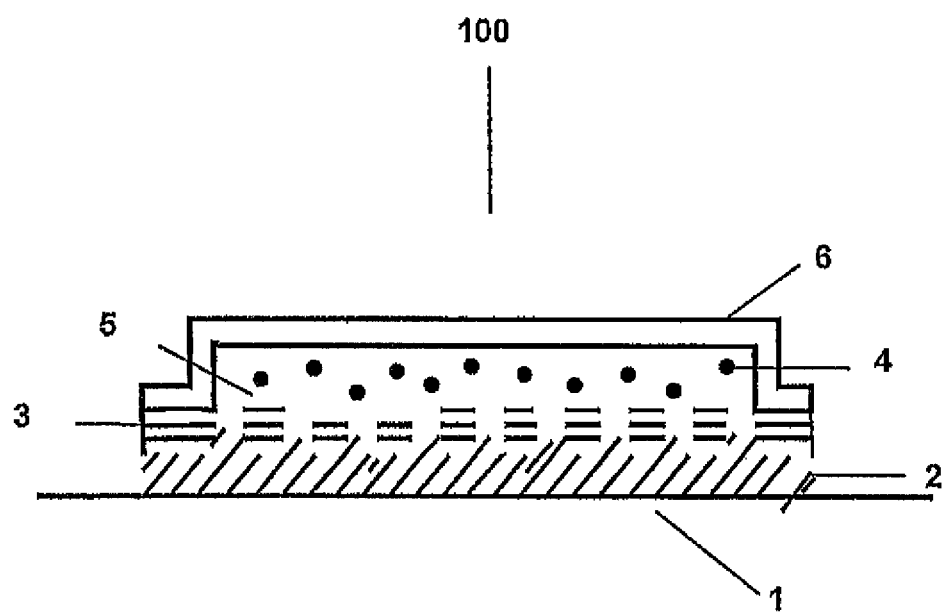

RESERVOIR SYSTEM WITH CLOSED MEMBRANE

FIELD OF THE INVENTION

The present invention relates to a dermal or transdermal therapeutic system comprising a reservoir that contains at least one active substance, a membrane which delimits the active substance reservoir and is permeable to the active substance, and a closing layer which is impermeable to the active substance at temperatures below the skin temperature while being permeable to the active substance at temperatures at, or above, the skin temperature.

DISCUSSION OF PRIOR ART

Therapeutic systems for administering active substances by way of absorption through the skin (dermal or transdermal administration) have become highly important over recent decades. An ever-growing number of dermally or transdermally applicable medicaments have been discovered. The advantage of this form of administration is that active substances migrate into the blood vessels while evading the gastrointestinal tract. Thus, passage through the hepatic system is avoided before the active substance has reached its destination.

The aforementioned systems, such as plasters, can be categorized with regard to their mode of operation into two main groups: the so-called matrix systems and the reservoir systems. Those in the first group contain the active substance or active-substance formulation in the adhesive layer. Those in the second category are systems which contain the active substance or active-substance formulation in a reservoir, that is, in the filling material in which the active substance, in dispersed form, is usually present. The filling material of the reservoir system can consist of a polymer or a liquid, or both. To avoid a leakage of the active substance-containing liquid, dermal or transdermal therapeutic systems of the reservoir type are usually delimited by an active substance-permeable membrane which is provided with an adhesive layer facing the skin. Such systems are described in U.S. Pat. No. 4,379,454, WO 03/011 291, EP 0 366 240, as well as DE 689 29 533.

In spite of many advantages, known reservoir systems also have disadvantages. In most cases, due to low stability of the skin-facing adhesive layer in the presence of liquids, storage stability is often a problem. Instability of the adhesive layer due to contact with liquids can lead to leakage from the reservoir and, thus, to an unusable system. Furthermore, the skin-facing adhesive layer represents an additional barrier to active substance permeation and can be a performance restricting factor, particularly for active substances that are needed in high dosages. In the case of highly potent active agents with narrow therapeutic indices, the accumulation of the active substance in the adhesive layer can lead to an undesirably high initial release of the active agent after the application of the system. Furthermore, with numerous active agents often unstable in the presence of oxygen, and with the terminal adhesive layer allowing the active agent access to oxygen, these systems only have a short durability.

EP 0 273 004 describes a transdermal or topical system in which activating agents initiate the release of the active substance. In one embodiment, the barrier between the skin and the active-substance layer can be modified. In this embodiment, the permeable membrane is a xerogel or an ionic gel, which is permeable to the active substance or constituents of the active substance formulation only in their hydrated form. This system comprises an additional compartment containing water or a buffer solution which, after activation, causes hydration of the xerogel or an increase in water content, thereby making the pores of the membrane permeable to the active agent. Crosslinked polyacrylates and bases are mentioned as examples of membrane materials and active agents, respectively. This embodiment is extremely elaborate to manufacture and the functional mechanism leads to release kinetics that are difficult to reproduce most of the time.

SUMMARY OF EMBODIMENTS OF THE INVENTION

It is a purpose of the present invention to provide improved dermal or transdermal therapeutic systems without the aforementioned disadvantages.

This improvement is achieved by the present invention which comprises a reservoir containing at least one active substance, a membrane which delimits the active substance reservoir and is permeable to the active substance, and a closing layer which is impermeable to the active substance at a temperatures below the skin temperature and is permeable to the active substances at temperatures at, or above, the skin temperature. "Below skin temperature" refers to the temperature of the human skin, which can vary depending on the individual and environmental conditions, and ranges from about 30° C. to about 35° C. In particular, the skin temperature lies in the range from 31 to 33° C., and is nominally about 32° C.

Embodiments of the present invention make it possible to produce dermal and transdermal therapeutic systems that have higher storage stability and, thus, higher product safety. In doing so, such embodiments widen the range of active substances suitable for use in these systems.

Since a system according to the invention does not have an additional adhesive layer on the skin-facing side of the membrane, it is possible to administer active substances in higher dosages.

Another advantage of a system according to the invention relates to the manufacture of dermal or transdermal systems in which the active substance is prevented from accumulating in the adhesive layer during storage, thereby avoiding an undesirably high initial release of the active substance.

The dermal or transdermal therapeutic system according to embodiments the invention comprises the following components, which may be of the same or different sizes: a closed cover layer impermeable to the constituents of the active-substance formulation; a liquid or solid reservoir layer comprising one or a plurality of active substances, where the active substance-containing reservoir is delimited by an active substance-permeable membrane; and a closing layer on the reservoir membrane at the side of the skin to which the system is to be applied. In principle, it is possible that the reservoir matrix is present in the form of a liquid, or a gel, or a self-supporting solid material. Of course, in the case of a liquid or fluent matrix, a person skilled in the art can make appropriate provisions to avoid "leaking" of the matrix or of the contained active substance(s). Examples of this include the provision of a solid- or liquid-impermeable coating which is delimited by an active substance-permeable membrane on the skin-facing side, or the thickening of the matrix by means of suitable gelling agents. Preferably, the matrix is polymer based.

Usually, all polymers that are employed in the manufacture of transdermal systems, and which are physiologically harmless, are suitable for production of the reservoir matrix. The polymers can be selected from the group comprising cellulose derivatives such as ethyl cellulose, hydroxypropyl cellulose, carboxymethyl cellulose, polyethylenes, chlorinated polyethylenes, polypropylenes, polyurethanes, polycarbonates, polyacrylic acid esters, polyacrylates, polymethacrylates, polyvinyl alcohols, polyvinyl chlorides, polyvinylidene chlorides, polyvinyl pyrrolidones, polyethylene terephthalates, polytetrafluoro ethylenes, ethylene/propylene copolymers, ethylene/ethyl acrylate copolymers, ethylene/vinyl acetate copolymers, ethylene/vinyl alcohol copolymers, vinyl chloride/vinyl acetate copolymers, vinyl pyrrolidone/ethylene/vinyl acetate copolymers, rubber, rubber-like substances, synthetic homo-, co- or block-polymers, silicones, silicone derivatives, and mixtures thereof. Polymers with a basis of styrene-butadiene-styrene block-copolymers, polyisobutylene, among others, can be used.

The active substance-containing reservoir of the plaster can also comprise skin penetration enhancers, fillers (such as zinc oxide or silica), solubilizers, cross-linking agents, stabilizing agents, emulsifiers, preserving agents, antioxidants solvents, and mixtures thereof. Of course, a person skilled in the art can make provisions for the stability of the closing layer not being affected by the mentioned additives.

Where necessary, the system can be formed with a peelable protective film on the skin-facing application surface.

When the system is applied to the skin, the closing layer is selectively converted from an impermeable state to a permeable state. Contact with the skin increases the temperature of the closing layer, which causes an increase in the permeability of the closing layer. This results in a release of the active substance through the active substance-permeable membrane and into the skin. In other instances, the closing layer can function as a permeation enhancer and accelerate the release of the active substance. The closing layer, which is impermeable at temperatures below the skin temperature, is preferably impermeable to oxygen.

The closing layer can be self-adhesive for the purpose of fixing the surface of the system to the skin.

To improve the stability of active agents that are susceptible to oxidative decomposition, the closing layer can be provided with one or several antioxidants.

The carrier layer or cover layer of the plaster is preferably impermeable and inert to the substances contained in the active substance-containing layer, the adhesive layer and, in particular, the active substance. This layer can be based on polymers such as polyester and polyethylene terephthalate, polyolefins such as polyethylenes, polypropylenes, polybutylenes, polycarbonates, polyethylene oxides, polyurethanes, polystyrenes, polyamides, polyimides, polyvinyl acetates, polyvinyl chlorides, polyvinylidene chlorides, or copolymers such as acrylonitrile/butadiene/styrene copolymers, which can possibly comprising paper fibers, textile fibers, and mixtures thereof. If needed, this layer can be metallized or pigmented. The carrier layer or cover layer of the plaster can also consist of a combination of a metal foil and a polymer layer. The thickness of the carrier layer is preferably about 3 μm to about 100 μm.

In an alternative embodiment, the system can be fixed to the skin by means of a cover plaster (overtape).

BRIEF DESCRIPTION OF THE DRAWING

The invention is further described below by means of the subsequent detailed description of advantageous embodiment examples of the invention, reference being made to accompanying drawing, wherein:

FIG. 1 is a cross sectional a view of an exemplary embodiment of the invention.

DETAILED DESCRIPTION OF EMBODIMENTS OF THE INVENTION

As shown in FIG. 1, an embodiment of the invention is a plaster in the form of a liquid-filled reservoir system 100 with a limiting active substance-permeable membrane and a closing layer. Lowermost layer 1 is a peelable protective layer which is removed before the system is applied to the recipient's (or the patient's) skin. The applicable plaster is fixed to the skin as a whole. Closing layer 2 on the side of the skin is connected with the active substance-permeable membrane 3 and faces the skin of the patient. Reservoir 5, which contains a matrix including active substance 4, is limited on the skin-averted side by impermeable cover layer 6. Cover layer 6 is connected with membrane 3 or, preferably, welded thereto at the edges, as shown.

The described structure, transdermal application system 100, serves to transport one or more active substances 4, which are contained in reservoir 5, through active substance-permeable membrane 3, subsequent skin-facing closing layer 2, and onto the skin surface on which the system is fixed. The active substance is delivered in a therapeutically sufficient, or effective, concentration and in a controlled manner over a long period of time.

Examples of suitable active agents include analgetics, μ-opioid-receptor-antagonists, anaesthetics, parasympathomimetics, parasympatholytics, antiemetics, emetics, sympathomimetics, hormons, anti-migraine agents, antiallergics, anticonvulsants, anti-dementia agents, antidepressants, beta blockers, alpha blockers, and analeptics.

The analgetics can be opioids, among which the full agonists, the mixed agonists/antagonists, the partial antagonists, and the full antagonists can be mentioned. Examples of full agonists are fentanyl, remifentanil, oxycodone, and methadone. Among the full antagonists, naloxone and naltrexone are examples. An example of an agonist/antagonist is nalbuphine, and an example of a partial antagonist is buprenorphine. Salicylic acid derivatives such as acetylsalicylic acid, etofenamate, or diclofenac are examples of acidic analgetics.

Of the μ-opioid-receptor-antagonists, almivopan and methylnaltrexone are examples.

Among the anaesthetics, local anaesthetics such as lidocaine, tetracaine, or etidocaine are to be considered.

Examples of parasympathomimetics are the cholinesterase inhibitors, and among them particularly physostigmine, rivastigmine, neostigmine, donepezil, and galantamine can be used.

Among the parasympatholytics, scopolamine is an example.

The antiemetics can be selected from the parasympatholytics, 5-$HT_3$-receptor-antagonists such as ondansetron and granisetron, and dopamine-$D_2$-receptor-antagonists such as domperidone.

Of the emetics, dopamine-$D_2$-receptor-agonists such as apomorphine are to be considered.

Among the sympathomimetics, the catecholamines such as dobutamine have to be considered. Furthermore, the β-2-sympathomimetics such as salbutamol, fenoterol, and clenbuterol are examples.

The hormones can be selected from among estradiol, norelgestromin, goserelin, and buserelin.

Examples of anti-migraine agents are 5-$HT_1$-receptor-agonists such as triptanes and, among those, zolmitriptan, sumatriptan, and naratriptan in particular are useful.

Tamsulosin can be mentioned as an example of an antagonist for alpha-1-adrenoreceptors. An example for anticonvulsants is gabapentin. Memantine can be mentioned as an example of an anti-dementia drug.

Among the antihistamines, the antiallergics such as mizolastine, triprolidine, and desloratadine come into consideration.

Among the antidepressants, nortriptyline is an example. Nebivolol is an example of a suitable beta blocker.

An example for an analeptic is methylphenidate.

The matrix can also contain more than one active substance, for example, a combination of two active substances, such as a parasympathomimetic in combination with a parasympatholytic, in particular physostigmine/scopolamine, an analgetic in combination with an antiemetic such as fentanyl in combination with granisetron, or two analgetics such as a μ-receptor-agonist and a μ-receptor-antagonist, like fentanyl/naloxone.

The system according to the invention is particularly preferred for use with active substances that exhibit temperature instability and for which storage temperatures below 26° C., in particular, temperatures in the range of about 2° C. to about 8° C., are recommended.

According to the present application, the closing layer is understood to be a layer which is impermeable to the matrix substances at temperatures below the skin temperature and is permeable to those substances at temperatures at, or above, skin temperature. Skin temperature is understood to be the temperature of the patient's skin, which can vary depending on the individual and environmental conditions, and ranges from about 30° C. to about 35° C. In particular, the skin temperature typically lies in the range of 31° C. to 33° C., and is generally about 32° C. In the system according to the invention, the closing layer material has a melting temperature in the range of the skin temperature, which is preferably in the range of about 30° C. to 35° C., and, in particular, in range of about 31° C. to about 33° C.

By selecting suitable components in the right proportions, mixtures of substances can also be used to set the desired melting temperature of the closing layer.

A substance for the closing layer can be selected from the group of vegetable fats, animal fats, fatty acids, alkanols, mono-, di-, and triglycerides of long-chain saturated fatty acids ($C_{12}H_{24}O_2$ to $C_{18}H_{36}O_2$), as well as medium-chain triglycerides ($C_6H_{12}O_2$ to $C_{12}H_{20}O_2$), esters of long-chain alcohols and acids, natural resins, high-molecular paraffines, polyethylene glycol derivatives of hydrated castor oil, polyethylene glycol derivatives of tocopherol, polysaccharides, and the polymers of acrylic acid. Particularly suitable are homogeneous mixtures from the aforementioned groups of substances.

Among the group of vegetable fats, cocoa butter, carnauba wax, cupuacu butter, candelilla wax, and shea butter can be used. Homogeneous mixtures of these vegetable fats can be advantageous.

Among the animal fats, beeswax and lanolin are examples. Spermaceti substitute can serve as a synthetic substitute for spermaceti.

Hard fats (adeps solidus) are examples of a compound of the mono-, di-, and triglycerides of long-chain saturated fatty acids ($C_{10}H_{20}O_2$ to $C_{18}H_{36}O_2$). From the group of the medium-chain triglycerides ($C_6H_{12}O_2$ to $C_{10}H_{20}O_2$), neutral oil comprising, in particular, the fatty acids octanoic acid or decanoic acid, or both, are suitable.

From the group of the alkanols, dodecanol, tridecyl alcohol, and cetyl alcohol are examples.

Undecenoic acid and stearic acid are examples of free fatty acids.

Among esters of long-chain alcohols and acids, palmitic acid myricyl ester can be mentioned.

Colophony is an example from the group of the natural resins. Examples of polysaccharides are xanthane, guar flour, and hyaluronic acid. Carbopol is an example for polyacrylic acid.

Tocophersolan is an example for a material of the polyethylene glycol derivative of tocopherol.

In the system according to an embodiment of the invention, the closing material can have a layer thickness of about 50 μm to about 600 μm and, in particular, from about 100 μm to about 500 μm. A layer thickness of about 200 μm to about 400 μm is particularly preferred.

The system according to the invention is characterized by the material of closing layer 2 having a basis of vegetable fat and animal fat. It is advantageous to add a natural resin to improve the adhesiveness of the system.

According to embodiments the invention, the closing layer material can have antioxidant properties, which is particularly relevant in the case of active substances that are oxidized in the presence of oxygen. Preferable in this regard are vegetable fats containing a proportion of antioxidants or those to which antioxidants have been added. Among the group of vegetable fats, cupuacu butter is particularly preferable and, in particular, palmitic acid myricyl ester. Tocophersolan can also be used as an antioxidant.

An embodiment of the invention is also characterized by a closing layer material with a basis of hard fat (adeps solidus) and neutral oil. The mixture of hard fat and neutral oil preferably comprises about 60% to about 90% by weight of hard fat and about 10% to about 40% by weight of neutral oil. Even more preferred, is a mixture of about 75% to about 90% by weight of hard fat and about 10% to about 25% by weight of neutral oil.

In the system according to embodiments of the present invention, the consistency of the closing layer material can be adjusted by the addition of a fatty acid. In this regard, it is advantageous to use as the fatty acid, undecenoic acid or stearic acid in a proportion of about 1-20% by weight. A proportion of about 5-10% by weight is particularly preferable. Furthermore, alkanols such as cetyl alcohol, tridecyl alcohol, or dodecanol can be added in a proportion of about 1-20% by weight, and preferably a proportion of about 5-10% by weight.

Furthermore, the closing layer material can consist of a polymer with an additive. Particularly preferable is polyacrylic acid with the polyethylene glycol derivative of hydrated castor oil as an additive.

The active substance-permeable membrane 3 of the reservoir system according to the invention preferably consists of an inert polymer, which is selected from among polyethylenes, polypropylenes, polyvinyl acetates, polyamides, ethylene/vinyl acetate copolymers and silicones. The thickness of the membrane is about 5 μm to about 100 μm, preferably between about 10 μm to about 50 μm, and more preferably between about 15 μm to about 40 μm.

The active substance-permeable membrane preferably has pores, the size of which ranges from about 0.1 μm to about 50 μm. The pores preferably have a size in the range of about 0.2 μm to about 10 μm, and more preferably in the range of about 0.5 μm to about 5 μm.

The system according to the invention can be provided with a foil 6 which serves as a cover plaster. The foil extends beyond the system at all sides and can be provided with a pressure-sensitive adhesive in at least a circumferential zone.

The releasable protective layer 1 of the reservoir system according to embodiments of the invention can consist of polyethylene, polyester, polyethylene terephthalate, polypropylene, polysiloxane, polyvinylchloride, or polyurethane and, if applicable, treated paper fibers, such as cellophane and, as the case may be, preferably have a coating of silicone, fluorosilicone, or fluorocarbon.

The dermal and transdermal therapeutic systems according to embodiments of the invention can generally be produced in a way as described for the following special exemplary embodiments (Examples 1 and 2).

EXAMPLE 1

For the production of closing layer 2, a mixture of hard fat (80% by weight) and neutral oil (20% by weight) are melted at 75° C. and maintained in liquid phase at 40° C. Palmitic acid myricyl ester is homogeneously worked therein in an amount of 2% by weight. The coating of active substance-permeable membrane 3 (in the present case the microporous polyethylene membrane DSM Solupor) is performed on a continuous coating machine by means of a knife coater in a thickness of 250 μm.

After being coated the membrane is cooled until the closing layer hardens at 4° C. For producing the reservoir system the coated membrane is welded at 175° C. and under pressure by maintaining a small filling opening, to a cover layer (backing foil) by means of a conventional seal machine, Tamsulosin Base (2% by weight) is dissolved in ethanol (75% by weight) and stirred to a homogeneous solution by adding 23% by weight of isopropyl myristate. Reservoir 5 is filled with the active substance-containing solution through the filling opening, welded, and punched out. The system is stored at 2° C. to 8° C. After the removal of the protective foil, the system is fixed to the skin by means of an adhesive-coated overtape.

EXAMPLE 2

For producing closing layer 2, a mixture of bees wax (70% by weight), carnauba wax (20% by weight), and colophony (10% by weight) are melted at 110° C. and maintained in liquid phase at 45° C., Tocophersolan is added in an amount of 5-10% by weight. The liquid mixture is stirred until it reaches homogeneity. The coating of the active substance-permeable membrane (in the present case, polypropylene Celgard 2400) is performed on a continuous coating machine by means of a knife coater at a thickness of 300 μm.

After being coated the membrane is cooled until the closing layer hardens (4° C.). For producing the reservoir system the coated membrane is welded, at 175° C. and under pressure by maintaining a small filling opening, to a cover layer (backing foil) by means of a conventional seal machine. Physostigmin base is dissolved in an ethanolic solution. Hydroxypropyl cellulose is added in a proportion of 2.5% by weight; the mixture is allowed to rest until the hydroxypropyl cellulose has completely swollen. The reservoir is filled with the active-substance-containing hydrogel through the filling opening, welded, and punched out. The system is stored at a temperature below 25° C. After the removal of the protective foil the system is affixed to the skin.

What is claimed is:

1. A dermal or transdermal therapeutic system prepared for applying to the skin of a patient, said therapeutic system comprising:
an active substance reservoir;
an active substance-permeable membrane which delimits the active substance reservoir on one side; and
a temperature dependent closing layer overlaying said membrane, said closing layer being impermeable to an active substance in said reservoir at a temperature lying below a skin temperature of the patient while being permeable to the active substance at or above the patient's skin temperature, said closing layer functioning as a switch, to be in the impermeable condition at temperatures below skin temperature, and switching to the permeable condition when said closing layer is applied to the skin of the patient, said closing layer consisting of a homogeneous mixture of materials consisting of beeswax and carnauba wax, with the proportion of beeswax being in the range of about 40 to 95% by weight and the proportion of carnauba wax being in the range of about 5 to 60% by weight.

2. The dermal or transdermal therapeutic system according to claim 1, wherein the closing layer has permeation-enhancing properties at skin temperature and above.

3. The dermal or transdermal therapeutic system according to claim 1, wherein the closing layer has pressure-sensitive adhesive properties.

4. The dermal or transdermal therapeutic system according to claim 1, wherein the thickness of the closing layer lies in the range of 50 μm to 600 μm.

5. The dermal or transdermal therapeutic system according to claim 1, wherein the thickness of the closing layer lies in the range of 100 μm to 500 μm.

6. The dermal or transdermal therapeutic system according to claim 1, wherein the thickness of the closing layer lies in the range of 200 μm to 400 μm.

7. The dermal or transdermal therapeutic system according to claim 1, wherein the active substance reservoir is formed as a solid, semi-solid, or liquid reservoir.

8. A dermal or transdermal therapeutic system comprising:
an active substance reservoir;
an active substance-permeable membrane which delimits the active substance reservoir; and
a closing layer, the closing layer being impermeable to an active substance at a temperature lying below a skin temperature while being permeable to the active substance at skin temperature or above, wherein the closing layer comprises 0.1 to 10% by weight of antioxidants, wherein the antioxidants are polyethylene glycol derivatives of tocopherol.

9. The dermal or transdermal therapeutic system according to claim 8, wherein the closing layer comprises a material selected from the group consisting of vegetable fats and animal fats and mixtures thereof.

10. The dermal or transdermal therapeutic system according to claim 8, wherein the closing layer comprises a material selected from the group consisting of cocoa butter, cupuacu butter, carnauba wax, candelilla wax, shea butter, lanolin, beeswax, hard fat, neutral oil, colophony, and mixtures thereof.

11. The dermal or transdermal therapeutic system according to claim 8, wherein the closing layer comprises a material selected from the group consisting of mixtures of vegetable fats and animal fats and mixtures of vegetable fats and animal fats in combination with resins.

12. A dermal or transdermal therapeutic system prepared for applying to the skin of a patient, said therapeutic system comprising:
an active substance reservoir;
an active substance-permeable membrane which delimits the active substance reservoir on one side; and
a temperature dependent closing layer overlaying said membrane, said closing layer being impermeable to an active substance in said reservoir at a temperature lying below a skin temperature of the patient while being permeable to the active substance at or above the patient's skin temperature, said closing layer functioning as a switch, to be in the impermeable condition at temperatures below skin temperature, and switching to the permeable condition when said closing layer is applied to the skin of the patient, said closing layer comprising 0.1 to 10% by weight of antioxidants, said antioxidants being polyethylene glycol derivatives of tocopherol.

* * * * *